United States Patent
Chauvin et al.

(10) Patent No.: US 10,751,270 B2
(45) Date of Patent: Aug. 25, 2020

(54) GEL BASE IN THE FORM OF A TRANSLUCENT GEL WITHOUT TRIETHANOLAMINE

(71) Applicants: SUDCOSMETICS, Paris (FR); LABORATOIRE SANDRALEX, Peypin (FR)

(72) Inventors: Alex Chauvin, Nans les Pins (FR); Laurent Dodet, Saint Jean de Muzols (FR); Jean-Marie Total, Carqueiranne (FR)

(73) Assignees: SUDCOSMETICS, Paris (FR); LABORATOIRE SANDRALEX, Peypin (FR)

( * ) Notice: Subject to any disclaimer, the term of this patent is extended or adjusted under 35 U.S.C. 154(b) by 0 days.

(21) Appl. No.: 15/547,623

(22) PCT Filed: Jan. 25, 2016

(86) PCT No.: PCT/FR2016/050143
§ 371 (c)(1),
(2) Date: Dec. 27, 2017

(87) PCT Pub. No.: WO2016/120552
PCT Pub. Date: Aug. 4, 2016

(65) Prior Publication Data
US 2018/0104164 A1    Apr. 19, 2018

(30) Foreign Application Priority Data

Jan. 30, 2015  (FR) ..................... 15 50750

(51) Int. Cl.
| A61K 8/04 | (2006.01) |
| A61Q 9/02 | (2006.01) |
| A61K 8/36 | (2006.01) |
| A61K 8/19 | (2006.01) |
| A61K 8/34 | (2006.01) |
| A61K 8/73 | (2006.01) |

(52) U.S. Cl.
CPC .............. *A61K 8/361* (2013.01); *A61K 8/042* (2013.01); *A61K 8/19* (2013.01); *A61K 8/34* (2013.01); *A61K 8/345* (2013.01); *A61K 8/731* (2013.01); *A61Q 9/02* (2013.01); *A61K 2800/262* (2013.01); *A61K 2800/30* (2013.01)

(58) Field of Classification Search
None
See application file for complete search history.

(56) References Cited

U.S. PATENT DOCUMENTS

| 1,771,707 A * | 7/1930 | Doran ...................... C11D 9/16 |
| | | 424/73 |
| 4,026,818 A | 5/1977 | Ciaudelli |
| 5,248,495 A * | 9/1993 | Patterson ............... A61K 8/042 |
| | | 424/47 |
| 2006/0093689 A1* | 5/2006 | Kawada .................. A61K 8/63 |
| | | 424/771 |
| 2013/0161349 A1* | 6/2013 | Pfeiffenberger ........ B32B 15/20 |
| | | 222/95 |

FOREIGN PATENT DOCUMENTS

| EP | 0284765 A2 | 10/1988 |
| WO | 2014177189 A1 | 11/2014 |

* cited by examiner

*Primary Examiner* — Jennifer A Berrios
(74) *Attorney, Agent, or Firm* — Browdy and Neimark, PLLC

(57) ABSTRACT

The invention relates to a new composition in the form of a translucent, advantageously transparent, gel, without triethanolamine, comprising at least
  a fatty body in the form of an oleic acid
  an aqueous phase; and
  a base or a mixture of bases.
The invention also relates to compositions, advantageously cosmetic compositions, comprising said gel base, such as a shaving gel.
The invention also relates to a method for preparing said gel base, a shaving method, the use of said gel base and a shaving kit.

26 Claims, No Drawings

GEL BASE IN THE FORM OF A TRANSLUCENT GEL WITHOUT TRIETHANOLAMINE

The present invention falls within the field of compositions, advantageously cosmetic compositions, that assume the form of a gel and that can be translucent, advantageously transparent, and that will also be called "gel base" in this text. Said "gel base" can be used directly without the addition of any other ingredients, but may advantageously be included in the formulation of any type of composition, for example cosmetic, pharmaceutical, dermatological, veterinary, hygienic, etc. compositions. The invention thus targets not only said gel base, but also any composition that may comprise said gel base.

According to the invention, "translucent" means that the gel base is able to allow rays of light to pass, but does not allow the contours or colors of the objects to be distinguished clearly.

According to the invention, "transparent" means that said gel base is able to allow light to pass while not shielding one's vision.

Gels are currently one of the most sought after cosmetic presentations. A gel is a solid that may have properties ranging from wet and ductile to hard and brittle; they form when molecules in solution bond in an array that traps a solvent.

While they are transparent and adhesive for hairstyling, they are soft to the touch when used in a cream. The gel can be a soft solid, easy to deform, resilient or plastic. The elasticity of the gels reinforces their adhesive power on solid surfaces.

A gel base is generally produced by saponification reaction from fatty bodies (triglycerides and/or fatty acids) and a base at a temperature comprised between 50° C. and 100° C. at atmospheric pressure or under pressure in an autoclave between 100° C. and 130° C.

A gel base may, owing to the addition of certain additives, be translucent, or even transparent. Thus, for example, shaving gels, or shower gels, can assume the form of a translucent, or even transparent, gel.

The base commonly used for saponification in order to obtain translucent, or even transparent, compositions is triethanolamine (in this respect, see "Cosmetologie Masculine" by Marie Claude Martini [Editions tec et doc/em inter/lavoisie]2009, or patent EP 0,294,010 B1 by the company NEUTROGENA).

However, triethanolamine is known as an additive that causes skin irritation, among other things, and is recognized as being moderately allergenic, oxidizing, and potentially able to lead to the formation of carcinogenic derivatives (nitrosamines).

Exposure to triethanolamine or its fumes may cause irritation of the skin, eyes and respiratory system. Repeated or prolonged exposure to this product may have a lipid-removing action on the skin. Triethanolamine may also cause redness, chapping and peeling.

Triethanolamine further has the particularity of forming, in the presence of nitrosating agents (nitrates, nitrogen oxides, etc.), nitrosamines, which are carcinogenic compounds. Although the law recommends avoiding introducing these "nitrosamine precursors" and nitrosating agents into a same formula, and given that, even in case of accidental contamination, this reaction is very slow, it appears desirable to eliminate the use of triethanolamine, which is also perfectly in line with the current trend advocating the use of the most natural products possible.

For these reasons, it is therefore of interest to be able to obtain a translucent gel base, advantageously transparent, that does not contain triethanolamine.

To achieve this result and thus resolve the drawbacks set out above, the applicant has surprisingly discovered that it was possible to obtain a gel base that is translucent, or even transparent, and that does not comprise triethanolamine.

The present invention therefore relates to a translucent, advantageously transparent, gel base, without triethanolamine, able to comprise at least
 a fatty body in the form of an oleic acid
 an aqueous phase; and
 a base or a mixture of bases.

This translucent, advantageously transparent, gel base can be used in any composition that may assume gel form, for example cosmetic, pharmaceutical, dermatological, veterinary, hygienic, etc. compositions, particularly cosmetic compositions, such as shower gels, bath products, shaving gels, skin products, hairstyling gels or shampoos. Preferred compositions comprising a gel base according to the invention are compositions intended for shaving. These compositions therefore will not have the drawbacks of those known from the prior art containing triethanolamine.

According to the invention, "without triethanolamine" means "which does not comprise triethanolamine", particularly as an essential component of the gel base. It is thus understood that the applicant wishes to propose a composition whose proposed formulation is free of triethanolamine. It must, however, be understood that according to the invention, it is the gel base that is free of triethanolamine and that whenever possible, any composition comprising a gel base without triethanolamine according to the invention, and if possible without added triethanolamine, falls within the scope of the invention. Unfortunately, it must be understood that compositions comprising a gel base without triethanolamine, but able to contain traces of triethanolamine accidentally added by a non-essential ingredient of the final composition, fall within the scope of the invention.

According to the invention, a gel refers to a homogeneous, isotropic, rigid, vibrating and resilient medium, as defined by Jean PORE in Microemulsions et Emulsions Multiples (Editions Etig, 1992), i.e., a solution stretched in balance with a crystal.

According to the invention, said fatty body can be a mixture of fatty bodies comprising at least oleic acid and at least one fatty body other than oleic acid.

Thus, in the continuation of the text, "fatty body", without other descriptor, must be understood as oleic acid used alone or as a mixture of oleic acid and at least one fatty body other than oleic acid.

According to the invention, said fatty body other than oleic acid can be any saturated or mono- or poly-unsaturated fatty body, known and usable according to the invention, advantageously a fatty body including fatty chains comprising from 6 to 30 carbon atoms, preferably from 8 to 20 carbon atoms.

Examples of a fatty body other than oleic acid usable according to the invention for example include triglycerides, oils, such as copra oil, palm oil, palm kernel oil, olive oil, sweet almond oil, babassu oil, fatty acids, in particular a mixture of headless copra oil fatty acids.

Advantageously, according to the invention, said fatty acid other than oleic acid can be a mixture of headless copra oil fatty acids.

Of course, according to the invention, said fatty body may be oleic acid used alone or in the form of a mixture of oleic acid and one or several other fatty bodies, other than oleic acid, in any proportion and in any quantity.

Preferably according to the invention, it is possible to use, as fatty body other than oleic acid, copra oil, particularly a mixture of headless copra oil fatty acids. Thus, according to the invention, it is more preferably possible to use a mixture of headless copra oil fatty acids, in any proportion and in any quantity.

According to the invention, said fatty body can be used in a quantity comprised between 1 wt % and 45 wt % relative to the total weight of the gel base, preferably in a quantity comprised between 2 wt % and 30 wt % relative to the total weight of the gel base, still more preferably in a quantity comprised between 4 wt % and 22 wt % relative to the total weight of the gel base.

Still according to the invention, the mixture of copra oil fatty acids can be "headless", i.e., it may have undergone a process seeking to decrease, or even eliminate, the chains with 6, 8 and/or 10 carbons (C6, C8 and C10), in order to make said fatty acids less irritating and less odiferous. Examples of a mixture of headless copra oil fatty acids include those marketed by the company Pacific Oleo (Pacific Oleochemicals Sdn Bhd (64175-U)—Plo 285, Jalan Pekeliling timur—PO Box 143, 81707 Pasir Gudang—Johor Darul Takzim, Malaysia).

According to one preferred form of the invention, it is possible to use a mixture of headless copra oil fatty acids and oleic acid, the ratio between the quantity of copra oil fatty acids and the quantity of oleic acid being able to be comprised between 5-1 and 1-5, advantageously 1-1.

Still according to the invention, the base may be chosen from among strong bases and weak bases or a mixture thereof, in any proportion and in any quantity.

Any base, strong or weak, known from the prior art can be used according to the invention. Examples include, but are not limited to, potash, sodium hydroxide, amino alcohols, sodium carbonate, potassium carbonate, or alkaline solutions (solution whose pH is greater than 7), advantageously those with a base of sodium hydroxide and/or potassium.

Preferably according to the invention, sodium hydroxide or potash will be used, still more preferably a mixture of potash and sodium hydroxide.

According to the invention, the base or the base mixture may be in a quantity comprised between 0.1 wt % and 25 wt %, advantageously between 0.15 wt % and 15 wt %, still more advantageously between 0.2 wt % and 10 wt % relative to the total weight of the gel base.

According to one particular form of the invention, when a mixture of potash and sodium hydroxide is used, the ratio between the quantity of potash and the quantity of sodium hydroxide can be comprised between 98/2 and 2/98, advantageously between 95/5 and 5/95.

When, according to the invention, one wishes to obtain a translucent gel base, the ratio between the quantity of potash and the quantity of sodium hydroxide can be comprised between 98/2 and 60/40.

The viscosity of the gel base according to the invention can be greater than 5000 mPa·s, preferably than 50,000 mPa·s and more preferably than 80,000 mPa·s. Preferably, it may be less than 900,000 mPa·s. This viscosity can be measured in ambient temperature (25° C.) and ambient pressure, using a Brookfield RV DV I Prime Viscosimeter with a helipath S94 spindle and at a speed of 2.5 revolutions/minute.

One preferred gel base according to the invention may comprise:
A mixture of headless copra oil fatty acids in a quantity comprised between 5 wt % and 8 wt %, advantageously between 6 wt % and 7 wt % relative to the total weight of the gel base;
Oleic acid in a quantity comprised between 10 wt % and 20 wt %, advantageously between 14 wt % and 15 wt % relative to the total weight of the gel base;
Potash, advantageously at 100%, in a quantity comprised between 1 wt % and 9 wt %, advantageously between 3 wt % and 5 wt % relative to the total weight of the gel base;
Sodium hydroxide, advantageously at 100%, in a quantity comprised between 0.1 wt % and 1 wt %, advantageously between 0.2 wt % and 0.5 wt % relative to the total weight of the gel base; and
water in a sufficient quantity to reach 100% of the total weight of the gel base.

The invention also relates to a method for preparing the gel base according to the invention, characterized in that
In a first step, the fatty body or bodies is (are) mixed in water brought to a temperature comprised between 50° C. and 60° C., and the mixture is homogenized by bringing the temperature to a temperature comprised between 55° C. and 65° C., advantageously 60° C.;
In a second step, one adds, to the mixture obtained in the first step, kept at temperature, the base or the mixture of bases, and this is homogenized for a length of time comprised between 20 and 50 minutes, preferably between 25 and 45 minutes.

To obtain the best possible results in terms of texture and transparency, it is important to respect the manufacturing method explained above as closely as possible.

The gel base according to the invention has the advantage of not comprising triethanolamine, and only comprising, at least for the majority, natural elements.

The gel base thus obtained can be used to prepare any desired composition, for example a cosmetic, pharmaceutical, dermatological, veterinary, hygienic, etc. composition, advantageously a cosmetic composition, particularly any cosmetic composition intended for shaving, for example a shaving gel.

The invention therefore also relates to a composition, advantageously a cosmetic composition, comprising at least one gel base according to the invention.

The invention thus also relates to a composition, advantageously a cosmetic composition, comprising at least one gel base according to the invention and any other additive, for example a gelling agent and/or a surfactant and/or any other additive typically used by one skilled in the art in the compositions according to the invention.

According to the invention, the gelling agent used to obtain the desired viscosity may be chosen from among synthetic gelling agents, for example, but not limited to, acrylates or natural gelling agents such as, but not limited to, gums, for example guar gum, gum arabic, adragant gum, *cassia* gum (*Cassia tora* and *Senna obtusifolia*), shellac, karaya gum, tara gum or gellan gum, gelatin, pectins such as those obtained from seeds and/or zests from gooseberries, apples, quince and/or citruses, alginic acid and derivatives thereof (conjugated base, salts and esters) alginates such as those obtained from algae in the laminaria or fucus families, carrageenans such as those extracted from *Kappaphycus alvarezii, Eucheuma denticulatum, Chondrus crispus, Betaphycus gelatinum Gigartina skottsbergii, Sarcothalia crispata, Mazzaella laminaroides, Gigartina canaliculata,*

*Hypnea musciformis, Mastocarpus stellatus,* or *Iridaea cordata,* agar-agar such as those obtained from the species *Gelidium, Gracilaria, Gracilariopsis, Gelidiella, Pterocladia,* or *Pterocladiella,* starch, a cellulose such as microcrystalline cellulose, cellulose powder, methylcellulose, ethylcellulose, hydroxycellulose, hydroxypropylcellulose, hydroxypropylmethylcellulose, ethylmethylcellulose, carboxymethylcellulose or a mixture thereof.

Advantageously, the gelling element may be a gum or a cellulose, and more advantageously a cellulose. According to the invention, the gelling agent may be in a quantity comprised between 0.02 wt % and 10 wt %, preferably between 0.05 w % and 5 wt %, and still more advantageously between 0.1 wt % and 1 wt % relative to the total weight of the composition.

According to the invention, a surfactant may be used to promote foaming of the composition or for its cleansing or emulsifying properties. According to the invention, said surfactant may be any surfactant known by those skilled in the art, as long as it can be used in the desired composition.

According to the invention, said surfactant may be chosen from among anionic surfactants having a negatively charged hydrophilic part, and zwitterionic or amphoteric surfactants, the hydrophilic part of which includes a positive charge and a negative charge, the global charge of which is zero, and the surfactants of which are nonionic.

Examples of anionic surfactants include, but are not limited to, alkyl-sulfates such as sodium or magnesium lauryl sulfates or alkyl-ether-sulfates such as lauryl-ether sulfates or sodium alkylethersulfate.

Examples of zwitterionic or amphoteric surfactants for example include, but are not limited to, substituted amino acids or betaine derivatives such as alkylbetaines such as cocoamidopropyl betaine, cocoamidopropyl hydroxysultaine or sodium cocoamphoacetate or imidazoline derivatives such as alkylimidazoline derivatives, cocoamidopropyl betaine, cocoamidopropyl hydroxysultaine or sodium cocoamphoacetate.

Examples of nonionic surfactants include, but are not limited to, polyethylene derivatives such as polyoxyethylene sorbitan stearate or lecithins, such as egg lecithin.

Advantageously according to the invention, said surfactant may be chosen, for information and non-limitingly, from among the mixture known as LAMESOFT® PO 65 (Coco-Glucoside and Glyceryl oleate) by the company BASF or LAMESOFT® OD (Coco-caprylate (and) lauryl glucoside (and) Glycerin (and) Polyglyceryl-2 Dipolyhydroxystearate (and) Polyglyceryl-3 diisostearate) by the company BASF.

According to the invention, said surfactant can be in a quantity comprised between 0.1 and the sufficient quantity to reach 100%, which means that the surfactant replaces the water. Advantageously according to the invention, said surfactant may be in a quantity comprised between 0.1 wt % and 10 wt %, still more advantageously between 2 wt % and 5 wt %.

According to the invention, a polyol may be used to favor transparency. According to the invention, as an example and non-limitingly, said polyol may be chosen from among ethyleneglycol or polyethylene glycols [diethylene glycol, triethylene glycol, propylene glycol, trimethylene glycol, butylene glycol, n-butylene glycol, 2,3-butylene glycol, secbutylene glycol, etc.], glycerol (glycerin), erythritol, xylitol, arabitol (lyxitol), ribitol (adonitol), sorbitol (gulitol), dulcitol (galactitol), mannitol, volemitol, maltitol, isomaltitol, lactitol (lactositol), aliphatic alditols or polyols (pentitols, hexitols, heptitols), ring cyclitols or polyols derived from cyclohexane or an alcohol such as, but not limited to, methanol, ethanol, propanol (n-propanol or propylic alcohol, propan-2-ol or isopropanol), butanol [1-butanol or n-butanol, 2-butanol or sec-butanol ((R)-butan-2-ol or (S)-butan-2-ol), isobutanol (2-methylpropan-1-ol), tert-butanol (2-methylpropan-2-ol)], pentanol [pentan-1-ol (normal amylic alcohol or n-amylic alcohol), 3-methylbutan-1-ol (isopentanol or isobutylcarbinol or iso-amylic alcohol), 2-methylbutan-1-ol (active amylic alcohol or secpentanol). 2,2-dimethylpropan-1-ol (neopentanol or neopentylic alcohol), pentan-3-ol diethyl carbinol), pentan-2-ol (sec-amylic alcohol or methyl (n) propyl carbinol), 3-methylbutan-2-ol (2-isopentanol or sec-isopentanol or methyl isopropyl carbinol), 2-methylbutan-2-ol (tert-Pentanol or dimethyl ethyl carbinol or tertiary amylic alcohol)], hexanol (hexan-1-ol, (RS)-hexan-2-ol, (RS)-hexan-3-ol, (RS)-2-methylpentan-1-ol, (RS)-3-methylpentan-1-ol, 4-methylpentan-1-ol, 2-methylpentan-2-ol, (RRSS)-3-methylpentan-2-ol, (RS)-4-methylpentan-2-ol, (RS)-2-methylpentan-3-ol, 3-methylpentan-3-ol, 2,2-dimethylbutan-1-ol, (RS)-2,3-dimethylbutan-1-ol, 3,3-dimethylbutan-1-ol, 2,3-dimethylbutan-2-ol, (RS)-3,3-dimethylbutan-2-ol, 2-ethylbutan-1-ol), heptanol and its isomers such as heptan-1-ol, fatty alcohols (octan-1-ol, 2-ethyl-1-hexanol, nonan-1-ol, decan-1-ol, undecanol, dodecan-1-ol or laurylic alcohol, tetradecanol or myristylic alcohol, hexadecanol or cetylic alcohol, octadecanol or stearylic acid, docosanol, policosanol, triacontanol or myricylic alcohol), aldols, ketols and acyloins.

The compositions according to the invention can also additionally contain a variety of additives, advantageously cosmetic additives, traditional to improve the esthetic qualities and the performance of these compositions, such as the gliding performance on the skin.

In this respect, examples in particular include:
  humectants, such as glycerin and sorbitol;
  emollients, such as plant oils;
  refreshing agents and soothing agents, such as menthol derivatives;
  lubricants, such as silicones, polyquaterniums;
  vitamins, such as vitamin D derivatives and vitamin E derivatives;
  dyes, such as UNICERT® synthetic dyes;
  perfumes, such as IFRA-certified perfume compositions and essential oils;
  antioxidants, such as tocophorerol;
  antibacterials and/or antifungals, such as potassium sorbate and sodium benzoate;
  preservatives, such as phenoxyethanol.

Of course, one skilled in the art will choose any additional compound(s) cited above and/or their quantities such that the advantageous properties intrinsically attached to the gel base according to the invention are not, or substantially are not, altered by the considered addition(s).

According to still another alternative of the invention, the compositions can further contain at least one agent that can promote the foaming and expansion of the gel, such as a liquefied gas such as, but not limited to, propane, butane, isobutane, pentane or isopentane, advantageously isobutane or isopentane that will be able to be used alone or in a mixture in a quantity comprised between 0.1 wt % and 20 wt % relative to the total weight of the composition, advantageously between 0.5 wt % and 10 wt %, very advantageously between 1 wt % and 3 wt %. Preferably, the liquefied gas can be a mixture of isobutane and isopentane that can be used in a ratio of quantity of isopentane to isopropane comprised between 99/1 and 1/99, advantageously 85/15 and 15/85, preferably 75/25.

Another object of the invention is a shaving gel comprising

A gel base according to the invention, in turn comprising between 6 wt % and 7 wt % relative to the weight of the gel base of a headless copra oil fatty acid mixture, between 14 wt % and 15 wt % relative to the weight of the oleic acid gel base, 4 wt % relative to the weight of the 100% potash gel base, 0.3 wt % relative to the weight of the sodium hydroxide gel base, said gel base making up 89% of the weight of the shaving gel composition;

A dye of the UNICERT® BLUE type for 0.000043% of the weight of the composition;

An emollient of the TEGOSOFT® LSE 65 K soft type (Evonik Industries AG Personal Care) for 2% of the weight of the composition;

An emollient such as polyglyceryl 1-4 caprate (TEGOSOFT® PC 41 by the company ADARA) for 0.5% of the weight of the composition;

Glycerin, like that sold by the company OLEON, for 2% of the weight of the composition;

Hydroxyethyl cellulose, like that sold by IMCD under the name NATROSOL® 250 HHR, for 0.75% of the weight of the composition;

A surfactant, such as the mixture known as LAMESOFT® PO 65 (Coco-Glucoside and Glyceryl oleate) by the company BASF, for 0.5% of the weight of the composition;

A surfactant, such as the mixture known as LAMESOFT® OD (Coco-caprylate, lauryl glucoside, Glycerin, Polyglyceryl-2 Dipolyhydroxystearate, Polyglyceryl-3 diisostearate) by the company BASF, for 0.9% of the weight of the composition;

SORBITOL E (QUIMASSO), for 3% of the weight of the composition;

A perfume for 1% of the weight of the composition;

Bisabolol (Brazilian natural Alpha Bisabolol by the company ELIXENS), for 0.1% of the weight of the composition; and Water in a sufficient quantity to reach 100%.

One skilled in the art will know, without difficulty, how to use the methods for manufacturing shaving gels to produce shaving gels according to the invention.

The shaving compositions according to the present invention can be packaged in any container, for example to be applied as is on the skin. They may in particular be packaged in any device making it possible to deliver a foaming gel, for example a device that can be a container provided with a pump or a pressurized container such as an aerosol or, and preferably, a container of the BOV (Bag On Valve) type, i.e., a container containing a pouch inside which the composition according to the invention is located, said pouch being surrounded inside said container by a gas whose role is to compress the pouch. Thus, the composition is never in contact with the gas allowing it to be expelled from the pouch.

The invention also relates to the use of a gel base as previously described to prepare a composition, advantageously a cosmetic composition.

The invention also relates to a shaving method, characterized in that a shaving gel as previously described is applied on the skin and one shaves. Said method may further comprise an additional step in which, after application of the composition according to the invention on the skin, the latter is massaged for several seconds to several minutes.

The invention lastly relates to a shaving kit comprising at least one shaving gel as previously described and optionally a razor.

Other advantages and properties of the invention will appear upon reading the following examples:

EXAMPLE 1: GEL BASE ACCORDING TO THE INVENTION

| | |
|---|---|
| Mixture of headless copra oil fatty acids (Pacific Oleo, Malaysia) | 6.5% |
| Oleic acid (Pacific Oleo, Malaysia) | 14.5% |
| 100% potash (BRENNTAG) | 4.0% |
| 100% sodium hydroxide (BRENNTAG) | 0.3% |
| Water | QSP 100% |

In a Jupiter-type mixer with a capacity of 100 Liters, the fatty acids (mixture of headless copra oil fatty acids and oleic acid) are mixed with water brought to 55° C. and the whole is homogenized by planetary-type agitation at 20 revolutions/minute. The temperature is then brought to 60° C. and the strong bases are then added. The assembly is then homogenized for about 35 minutes by planetary agitation at 15 revolutions/minute with turbine at 1000 revolutions/minute.

One thus obtains a gel base in the form of a translucent gel that can next be used in compositions, advantageously cosmetic compositions.

EXAMPLE 2: PREPARATION OF A SHAVING GEL

| | |
|---|---|
| Gel base of example 1 | 89.00% |
| UNICERT ® BLUE dye (05601-J (CAI42090), company LCW) | 0.43 10$^{-4}$% |
| TEGOSOFT ® LES 65 K soft (Evonik Industries AG Personal Care) | 2.0% |
| Glycerin (Natural Glycerin Codex, Company OLEON) | 2.0% |
| Hydroxyethyl cellulose (NATROSOL ® 250 HHR, company IMCD) | 0.75% |
| LAMESOFT PO 65 (company BASF) | 0.50% |
| SORBITOL E (QUIMASSO) | 3.0% |
| LAMESOFT OD (BASF) | 0.9% |
| TEGOSOFT PC 41 (company ADARA) | 0.5% |
| Perfume MAN PLUS (51419594, Expression Parfumée) | 1.0% |
| Brazilian natural Alpha Bisabolol (company ELIXENS) | 0.1%. |

The mixture of Natural Glycerin Codex and Hydroxyethyl cellulose (NATROSOL® 250 HHR) by homogenization and the gel base of example 1 is added to this preparation, in the preparation vat thereof at 60° C. under planetary agitation at 25 revolutions/minute with turbine at 1500 revolutions/minute until the gelling agent is perfectly dispersed.

The mixture of LAMESOFT PO 65 and SORBITOL E (QUIMASSO) is then added and homogenized for 10 minutes by planetary agitation at 25 revolutions/minute with turbine at 1500 revolutions/minute.

The LAMESOFT OD (BASF). TEGOSOFT PC 41 (company ADARA), MAN PLUS perfume and Brazilian natural Alpha Bisabolol (company ELIXENS) are then added under turbine at 1500 revolutions/minute, and the whole is homogenized for 10 minutes.

The whole is then left to cool to 40° C., under planetary agitation at 25 revolutions per minute with turbine at 1500 revolutions per minute.

A static mixer (PAMASOL) is then used to mix the obtained preparation with a combination of liquefied gases (2.2% of a 75% isopentane/25% isobutane mixture).

A transparent or translucent shaving gel is then obtained that can then be packaged in an aerosol of the Bag On Valve (LINDAL) type.

The invention claimed is:

1. A composition in the form of a translucent or transparent gel base, without triethanolamine, comprising at least:
   a fatty body in the form of oleic acid alone or a mixture of oleic acid and headless copra oil fatty acids, said fatty body being in a quantity between 4 wt % and 22 wt % relative to the total weight of the gel base;
   an aqueous phase; and
   a mixture of potash and sodium hydroxide in a quantity between 0.2 wt % and 10 wt % relative to the total weight of the gel base and wherein the ratio between the quantity of potash and the quantity of sodium hydroxide is between 98/2 and 60/40.

2. The gel base according to claim 1, wherein the fatty body is a mixture of headless copra oil fatty acids and oleic acid.

3. The gel base according to claim 1, comprising:
   headless copra oil fatty acids in a quantity between 5 wt % and 8 wt % relative to the total weight of the gel base;
   oleic acid in a quantity between 10 wt % and 20 wt % relative to the total weight of the gel base;
   potash in a quantity between 1 wt % and 9 wt % relative to the total weight of the gel base;
   sodium hydroxide in a quantity between 0.1 wt % and 1 wt % relative to the total weight of the gel base; and
   water in a sufficient quantity to reach 100% of the weight of the gel base.

4. A method for preparing the gel base composition of claim 1, comprising:
   in a first step, mixing the fatty body with water brought to a temperature between 50° C. and 60° C., and then the mixture is homogenized at a temperature between 55° C. and 65° C.;
   in a second step, adding the mixture of potash and sodium hydroxide to the mixture obtained in the first step and maintaining the temperature between 55° C. and 65° C.; and
   then the mixture obtained in the second step is homogenized for a length of time between 20 and 50 minutes.

5. A shaving composition or gel comprising at least one gel base as described in claim 1.

6. The composition according to claim 5, which is a cosmetic composition.

7. The composition according to claim 5, wherein the composition further comprises a gelling agent and/or a surfactant and/or a polyol and/or any other additive.

8. The composition according to claim 5, further comprising a liquefied gas or a liquefied gas mixture, chosen from among propane, butane, isobutane, pentane or isopentane.

9. The composition according to claim 8, wherein the liquefied gas or the liquefied gas mixture is in a quantity between 0.1 wt % and 20 wt % relative to the total weight of the composition.

10. A shaving gel comprising the gel base of claim 1, a dye, at least one emollient, glycerin, hydroxyethyl cellulose, at least one surfactant, sorbitol, a perfume and bisabolol.

11. The shaving gel according to claim 10, comprising:
    the gel base comprising:
        between 6 wt % and 7 wt % of headless copra oil fatty acids relative to the total weight of the gel base,
        between 14 wt % and 15 wt % of oleic acid relative to the total weight of the gel base,
        4 wt % of potash relative to the total weight of the gel base,
        0.3 wt % of sodium hydroxide relative to the total weight of the gel base and
        water QSP 100% relative to the total weight of the gel base,
    said gel base making up 89% based on the total weight of the shaving gel;
    a dye in a quantity of 0.000043% based on the total weight of the shaving gel;
    an emollient mixture in a quantity of 2.5% based on the total weight of the shaving gel;
    glycerin in a quantity of 2% based on the total weight of the shaving gel;
    hydroxyethyl cellulose, in a quantity of 0.75% based on the total weight of the shaving gel;
    a surfactant mixture in a quantity of 1.4% based on the total weight of the shaving gel;
    SORBITOL E in a quantity of 3% based on the total weight of the shaving gel;
    a perfume in a quantity of 1% based on the total weight of the shaving gel;
    bisabolol in a quantity of 0.1% based on the total weight of the shaving gel; and
    water in a sufficient quantity to reach 100% based on the total weight of the shaving gel.

12. A shaving composition or gel, according to claim 5, wherein shaving composition or gel is packaged in a container of the BOV (Bag On Valve) type.

13. A method for shaving, comprising applying a shaving gel according to claim 10 on the skin, and optionally massaging and shaving the skin.

14. A shaving kit comprising at least one shaving gel as described in claim 10 and optionally a razor.

15. The gel base according to claim 1, wherein the headless copra oil fatty acids are in a quantity between 6 wt % and 7 wt % relative to the total weight of the gel base.

16. The gel base according to claim 1, wherein the oleic acid is in a quantity between 14 wt % and 15 wt % relative to the total weight of the gel base.

17. The gel base according to claim 1, wherein the potash is in a quantity between 3 wt % and 5 wt % relative to the total weight of the gel base.

18. The gel base according to claim 1, wherein the sodium hydroxide is in a quantity between 0.2 wt % and 0.5 wt % relative to the total weight of the gel base.

19. The method for preparing a gel base according to claim 4, wherein, in the first step, the mixture is homogenized by bringing the temperature to a temperature of 60° C.

20. The method for preparing a gel base according to claim 4, wherein, in the second step, the mixture is homogenized for a length of time comprised between 25 and 45 minutes.

21. The composition according to claim 5, wherein the composition is a cosmetic composition intended for shaving.

22. The composition according to claim 21, wherein the cosmetic composition is a shaving gel.

23. The composition according to claim 8, wherein the liquefied gas or a liquefied gas mixture is chosen from among isobutane or isopentane.

24. The composition according to claim 8, wherein the liquefied gas or a liquefied gas mixture is a mixture of isobutane and isopentane.

25. The composition according to claim 9, wherein the liquefied gas or the liquefied gas mixture is in a quantity comprised between 0.5 wt % and 10 wt % relative to the total weight of the composition.

26. The composition according to claim 9, wherein the liquefied gas or the liquefied gas mixture is in a quantity comprised between 1 wt % and 3 wt % relative to the total weight of the composition.

* * * * *